United States Patent
Shaikh et al.

(10) Patent No.: US 11,794,176 B2
(45) Date of Patent: Oct. 24, 2023

(54) ANTIFOULING OLIGOMERIZATION CATALYST SYSTEMS

(71) Applicants: Saudi Arabian Oil Company, Dhahran (SA); Sumitomo Chemical Company, Limited, Chiba (JP)

(72) Inventors: Sohel Shaikh, Dhahran (SA); Motaz Khawaji, Thuwal Jeddah (SA); Hussain Al Yami, Thuwal Jeddah (SA); Wei Xu, Dhahran (SA)

(73) Assignees: Saudi Arabian Oil Company, Dhahran (SA); Sumitomo Chemical Company, Limited, Chiba (JP)

( * ) Notice: Subject to any disclaimer, the term of this patent is extended or adjusted under 35 U.S.C. 154(b) by 0 days.

(21) Appl. No.: 17/827,208

(22) Filed: May 27, 2022

(65) Prior Publication Data

US 2022/0280926 A1 Sep. 8, 2022

Related U.S. Application Data

(62) Division of application No. 15/181,923, filed on Jun. 14, 2016.

(60) Provisional application No. 62/181,955, filed on Jun. 19, 2015.

(51) Int. Cl.
*C07C 2/32* (2006.01)
*B01J 31/06* (2006.01)
*B01J 31/02* (2006.01)
*B01J 31/04* (2006.01)
*C07C 2/88* (2006.01)

(52) U.S. Cl.
CPC .......... *B01J 31/06* (2013.01); *B01J 31/0225* (2013.01); *B01J 31/0244* (2013.01); *B01J 31/0268* (2013.01); *B01J 31/04* (2013.01); *C07C 2/88* (2013.01); *B01J 2231/20* (2013.01); *C07C 2531/025* (2013.01); *C07C 2531/04* (2013.01); *C07C 2531/06* (2013.01); *C07C 2531/12* (2013.01); *C07C 2531/14* (2013.01); *C07C 2531/38* (2013.01)

(58) Field of Classification Search
None
See application file for complete search history.

(56) References Cited

U.S. PATENT DOCUMENTS

| | | |
|---|---|---|
| 2,738,151 A | 3/1956 | Herzog |
| 3,061,602 A | 10/1962 | Duck et al. |
| 3,686,350 A | 8/1972 | Yamada et al. |
| 4,242,531 A | 12/1980 | Carter |
| 4,484,016 A | 11/1984 | Maschmeyer et al. |
| 4,528,415 A | 7/1985 | Knudsen |
| 4,532,370 A | 7/1985 | LeQuan et al. |
| 4,538,018 A | 8/1985 | Carter |
| 4,606,854 A | 8/1986 | Ozawa et al. |
| 4,615,998 A | 10/1986 | Le Quan et al. |
| 5,292,837 A | 3/1994 | Heinrich et al. |
| 5,376,706 A | 12/1994 | Barsotti et al. |
| 5,494,171 A | 2/1996 | Kazamoto et al. |
| 5,728,912 A | 3/1998 | Saqualain Haider Rizvi et al. |
| 5,792,895 A | 8/1998 | Commereuc et al. |
| 5,811,618 A | 9/1998 | Wu |
| 5,856,612 A | 1/1999 | Araki et al. |
| 5,877,376 A | 3/1999 | Commereuc et al. |
| 6,184,428 B1 | 2/2001 | Zahoor et al. |
| 6,767,975 B1 | 7/2004 | Liu |
| 7,122,497 B1 | 10/2006 | Naqgy et al. |
| 7,157,532 B2 | 1/2007 | Payer et al. |
| 7,329,635 B2 | 2/2008 | Dickakian et al. |
| 7,361,623 B2 | 4/2008 | Dixon et al. |
| 7,638,597 B2 | 12/2009 | Etherton et al. |
| 7,919,569 B2 | 4/2011 | Xu et al. |
| 7,964,763 B2 | 6/2011 | Dixon et al. |
| 8,227,653 B2 | 7/2012 | Weber et al. |
| 8,252,871 B2 | 8/2012 | Aliyev et al. |
| 10,280,125 B2 | 5/2019 | Etherton et al. |
| 2003/0109766 A1 | 6/2003 | Commereuc et al. |
| 2007/0027276 A1 | 2/2007 | Cann et al. |
| 2013/0123443 A1 | 5/2013 | Siraux et al. |
| 2013/0303817 A1 | 11/2013 | Shaik et al. |
| 2014/0088331 A1 | 3/2014 | Axens |
| 2014/0250835 A1 | 9/2014 | Prabhu et al. |
| 2015/0141605 A1 | 5/2015 | Bradin |

(Continued)

FOREIGN PATENT DOCUMENTS

| | | |
|---|---|---|
| CN | 101189270 A | 5/2008 |
| CN | 102807632 A | 12/2012 |

(Continued)

OTHER PUBLICATIONS

Dawes et al. Journal of Polymer Science: Part A, 1964, 2, 3029-3051 (Year: 1964).*
International Search Report and Written Opinion dated Mar. 18, 2021 pertaining to International Application No. PCT/US2020/059974 filed Nov. 11, 2020, 13 pgs.
Notice of Allowance and Fee(s) Due dated Sep. 10, 2020 pertaining to U.S. Appl. No. 16/134,207, filed Sep. 18, 2018, 21 pgs.

(Continued)

*Primary Examiner* — Yun Qian

(74) *Attorney, Agent, or Firm* — DINSMORE & SHOHL LLP

(57) ABSTRACT

A catalyst system that may reduce polymeric fouling may include at least one titanate compound, at least one aluminum compound, and an antifouling agent. The antifouling agent may be chosen from one or more of a phosphonium or phosphonium salt; a sulfonate or a sulfonate salt; a sulfonium or sulfonium salt; an ester including a cyclic moiety; an anhydride; a polyether; and a long-chained amine-capped compound. The catalyst system may further include a non-polymeric ether compound.

14 Claims, No Drawings

(56) References Cited

U.S. PATENT DOCUMENTS

| | | |
|---|---|---|
| 2016/0367977 A1 | 12/2016 | Shaikh et al. |
| 2017/0197892 A1 | 7/2017 | Khawaji et al. |
| 2017/0274356 A1 | 9/2017 | Cann et al. |

FOREIGN PATENT DOCUMENTS

| | | |
|---|---|---|
| CN | 103665201 A | 3/2014 |
| CN | 103724149 A | 4/2014 |
| CN | 107778388 A | 3/2018 |
| EP | 0135441 A1 | 3/1985 |
| EP | 0181954 A1 | 5/1986 |
| EP | 0352856 A1 | 1/1990 |
| EP | 2738151 A1 | 6/2014 |
| JP | H02-1990-088529 | 3/1990 |
| RU | 2561921 C1 | 9/2015 |
| WO | 2013154446 A1 | 10/2013 |
| WO | 2015087303 A2 | 6/2015 |
| WO | 2015087304 A2 | 6/2015 |
| WO | 2015087305 A2 | 6/2015 |
| WO | 2015118462 A1 | 8/2015 |
| WO | 2017120310 A1 | 7/2017 |

OTHER PUBLICATIONS

Office Action dated Jan. 4, 2021 pertaining to U.S. Appl. No. 15/393,865, filed Dec. 29, 2016, 30 pgs.
Office Action dated Jul. 8, 2020 pertaining to Japanese Patent Application No. 2017-565808.
Office Action dated Aug. 10, 2020 pertaining to Singapore Patent Application No. 11201805653U.
Karin et al., "Removal of Trace Elemental Impurities from Polyethylene by Nitric Acid", Analytical Chemistry, vol. 47, No. 13, Nov. 1975, 4 pgs.
Extended European Search Report dated Dec. 20, 2019 pertaining to European Patent Application No. 19188473.3.
Office Action pertaining to RU2018128919 dated Feb. 27, 2020, 10 pgs.
Office Action dated Mar. 30, 2020 pertaining to U.S. Appl. No. 16/134,207, filed Sep. 18, 2018, 52 pgs.
Final Office Action dated Feb. 28, 2020 pertaining to U.S. Appl. No. 15/393,865, filed Dec. 29, 2016, 32 pgs.
Office Action dated Nov. 6, 2019 pertaining to Chinese Patent Application No. 201680035981.0.
Non-Final Office Action pertaining Io U.S. Appl. No. 15/830,800 dated Oct. 19, 2018.
P.S. Smith el al., "Ethylene dimerizalion over supported titanium alkoxides" Journal of Catalysis 105, pp. 187-198, 1987.
Al-Jaralla et al., "Part 1—Dimerization of Ethylene Io Butene-1", Catalysis Today 14, pp. 1-124, 1992.
Hennico et al., "Butene-1 is made from ethylene", Hydrocarbon Processing, vol. 69:3 (1990)—Abstract Only.
Luann Farrell, "Developments in Linear Alpha Olefin (LAO) Comonomer Technologies for Polyethylene", Luann M Farrell, ChemSystems PERP Program, May 2012.
International Search Report and Written Opinion pertaining to International Application No. PCT/US2018/051514 dated Jan. 8, 2019, 12 pages.
Office Action dated Jan. 11, 2019 pertaining to U.S. Appl. No. 15/393,865, filed Dec. 29, 2016.
Pietrzykowski et al., Reactions of methyl- and ethylaluminium compounds with alkoxyalcohols. The influence oof alkoxyalcohol substituents on the structure of the complexes formed, Inorganic Chimica Acta 334, 2002, pp. 385-394, Elsevier.
Invitation to Pay Additional Search Fees and Partial Search Report dated Sep. 15, 2016 for PCT Application No. PCT/US2016/037366 entitled "Antifouling Oligomerization Catalyst Systems".
International Search Report and Written Opinion pertaining to PCT/US2017/012299 dated Jun. 8, 2017.
Obrey et al., "A Lewis Base Promoted Alkyl/Alkoxide Ligand Redistribution: Reaction of [Me2Al(μ-OCPh3)]2 with IrHF", Organometallics, Nov. 1, 2001, vol. 20, No. 24, pp. 5119-5124.
T Mole, "Organoaluminium Compounds-XL Reaction of Trialkylaluminiums with Dialkylaluminium Alkoxides", Australian Journal of Chemistry, Jan. 1, 1966, pp. 381-386.
International Search Report pertaining to PCT/US2016/037366, filed Jun. 14, 2016, 9 pages.
Written Opinion pertaining to PCT/US2016/037366, filed Jun. 14, 2016, 9 pages.
Office Action dated Mar. 13, 2018 pertaining to U.S. Appl. No. 15/393,865.
International Search Report and Written Opinion dated Feb. 20, 2018 pertaining to International application No. PCT/US2017/064841.
Forestiere et al., "Oligomerization of Monoolefins by Homogenous Catalysts", Oil & Science and Technology—Review de Institue Francais du Petrole, pp. 663-664, vol. 64, No. 6, Nov. 2009.
Final Rejection pertaining to U.S. Appl. No. 15/393,865 dated Aug. 10, 2018.

* cited by examiner

ANTIFOULING OLIGOMERIZATION CATALYST SYSTEMS

CROSS-REFERENCE TO RELATED APPLICATIONS

This application is a Divisional Application of U.S. application Ser. No. 15/181,923 filed Jun. 14, 2016, which claims the benefit of U.S. Provisional Application Ser. No. 62/181,955 filed Jun. 19, 2015, each of which are incorporated by reference in their entireties herein.

BACKGROUND

Field

Embodiments of the present disclosure generally relate to catalyst systems used in ethylene oligomerization, and more specifically relate to antifouling catalyst systems used in ethylene oligomerization which may reduce undesired polymerization.

Technical Background

1-Butene and 1-hexene are important petrochemicals, especially for the production of polyethylene. The reaction of ethylene and other alpha-olefins, especially 1-butene and 1-hexene, forms various grades of linear low density polyethylene (LLDPE), a useful commercial polymer. A source of 1-butene is the butene fraction from the effluent of a hydrocarbon cracker, such as a steam cracker or fluidized catalytic cracker. However, the process for recovering 1-butene from such an effluent requires several difficult process steps that may make the process undesirable.

Several commercial processes selectively oligomerize ethylene into alpha olefins such as 1-butene and 1-hexene. A commercially successful dimerization process is the Alphabutol™ Process, developed by the Institute Francais du Petrole (IFP), described in A. Forestiere, et al., "Oligomerization of Monoolefins by Homogenous Catalysts", Oil & Science and Technology—Review de l'Institute Francais du Petrole, pages 663-664 (Volume 64, Number 6, November 2009). This process uses a bubble-point reactor that contains 1-butene as a process fluid to oligomerize ethylene selectively into 1-butene.

There is a known problem with oligomerization systems: polymer formation. Long residence times and poor heat removal from the highly exothermic reactions lead to the formation of polyethylene-based residues. A side effect of chronic fouling is increasingly frequent process shutdowns and higher maintenance costs for removing adhered polymer residues. Polymer residues may build layer upon layer and eventually close off openings and ports in locations with fluid flow. Additionally, a polymer coating along the wall of a reactor may act as an insulator, which may negatively affect heat transfer to the reactor system. Polymer can also collect debris that can be catalytically active or that can poison the reaction process.

An especially troublesome issue is the formation of "hot spots." A hot spot is an area where external cooling is ineffective and catalyst activity is high. It represents a loss of process control. A hot spot can be an area of collected polymer that includes catalytically active material that fosters side-reactions, including polymerization. If left unchecked, the hot spot can eventually lead to a process shutdown due to the loss of cooling capacity, a runaway polymerization reaction, or both.

SUMMARY

Accordingly, there is a continual need for effective methods to prevent polymeric fouling on reactor system walls and tubes while maintaining the desired oligomerization rate and selectivity to form reaction product.

According to one embodiment, a catalyst system that may reduce polymeric fouling may comprise at least one titanate compound, at least one aluminum compound, and an antifouling agent. The antifouling agent may be chosen from one or more of a phosphonium or phosphonium salt; a sulfonate or a sulfonate salt; a sulfonium or sulfonium salt; an ester comprising a cyclic moiety; an anhydride; a polyether; and a long-chained amine-capped compound. The catalyst system may further comprise a non-polymeric ether compound.

According to another embodiment, 1-butene may be selectively produced by a method that may comprise contacting ethylene with a catalyst system to oligomerize the ethylene to selectively form 1-butene. The catalyst system may comprise at least one titanate compound, at least one aluminum compound, and an antifouling agent. The antifouling agent may be chosen from one or more of a phosphonium or phosphonium salt; a sulfonate or a sulfonate salt; a sulfonium or sulfonium salt; an ester comprising a cyclic moiety; an anhydride; a polyether; and a long-chained amine-capped compound.

Additional features and advantages of the embodiments described in this disclosure will be set forth in the detailed description which follows, and in part will be readily apparent to those skilled in the art from that description or recognized by practicing the embodiments described, including the detailed description which subsequently follows, and the claims.

DETAILED DESCRIPTION

One or more embodiments of the present disclosure are directed to catalyst systems which may be utilized in promoting ethylene oligomerization, such as the dimerization of ethylene to form 1-butene or 1-hexene, while reducing reactor fouling caused by undesired polymerization. These catalyst systems are sometimes referred to in this disclosure as "antifouling ethylene oligomerization catalyst systems" or "antifouling catalyst systems". The antifouling catalyst systems described may comprise at least one titanate compound, at least one aluminum compound, and at least one antifouling agent. The antifouling catalyst systems may further comprise one or more non-polymeric ether compounds, and the components of the antifouling catalyst system may be mixed in a solvent such as hexane. The antifouling catalyst systems may be used to selectively oligomerize ethylene to produce 1-butene, while reducing undesirable polymerization, sometimes referred to in this disclosure as "fouling". For example, reactor fouling may occur due to the formation of solid polyethylene-based residues which may reduce fluid flow and fully block or at least partially block fluids in a reactor system from flowing at a desired rate. It should be understood that the "antifouling ethylene oligomerization catalyst systems" or "antifouling catalyst systems" described may not completely eliminate fouling during a reaction. However, these catalyst systems reduce fouling as compared with catalyst systems which do not include an antifouling agent as described in the present disclosure. Also, it should be understood that while the catalyst systems of the present disclosure may be useful in ethylene oligomerization reactions, such as ethylene dimerization to form 1-butene, they may also be useful for the catalysis of other chemical reactions, and the antifouling catalyst systems described in this disclosure should not be considered limited in their use to the dimerization of ethylene to 1-butene. It should further be understood that the antifouling agents described in this disclosure may be incorporated with other catalyst systems which contain, for example, non-titanium based catalysts.

As described previously in this disclosure, embodiments of the described antifouling catalyst systems may comprise one or more titanate compounds which may serve as a catalyst in the catalyst systems described in this disclosure. While several titanate compounds may be included in the antifouling catalyst system, in some embodiments a single titanate compound may be included in the antifouling catalyst system. In one or more embodiments, the titanate compound may be an alkyl titanate. An alkyl titanate may have the structure Ti(OR)$_4$ in which R is a branched or straight chain alkyl group. In one or more embodiments, each alkyl group may comprise from 2 to 8 carbons, where each R group may be the same or different. Suitable alkyl titanates may include tetraethyl titanate, tetraisopropyl titanate, tetra-n-butyl titanate (sometimes referred to as titanium butoxide or tetrabutyl orthotitanate), 2-tetraethylhexyl titanate, or combinations thereof. In one or more embodiments, the titanate compound of the antifouling catalyst system consists of tetra-n-butyl titanate.

As also described previously in this disclosure, embodiments of the described antifouling catalyst systems may comprise one or more aluminum compounds which may act as co-catalysts in the catalyst systems described in this disclosure. While several aluminum compounds may be included in the antifouling catalyst system, in some embodiments a single aluminum compound may be included. In one or more embodiments, one or more aluminum alkyl compounds may be included in the antifouling catalyst system. Aluminum alkyl compounds may have a structure of AlR'$_3$ or AlR'$_2$H, where R' is a straight chain or branched alkane comprising from 1 to 20 carbons, or an aluminoxane structure (that is, a partial hydrolysate of trialkylaluminum compounds). The R' groups of the aluminum alkyl compounds may be the same or different from one another. For example, and not by way of limitation, suitable aluminum alkyl compounds may include triethylaluminum, tripropylaluminum, tri-iso-butylaluminum, trihexylaluminum, or combinations thereof. In one or more embodiments, the aluminum compound of the antifouling catalyst system consists of triethylaluminum.

The antifouling catalyst systems described in this disclosure include at least one antifouling agent. An antifouling agent may be any additive to a catalyst system which decreases fouling by polymer production. Antifouling agents contemplated include phosphoniums or phosphonium salts, sulfonates or sulfonate salts, sulfoniums or sulfonium salts, esters, anhydrides, polyethers, and long-chained amine-capped compounds. It should be understood that as used in this disclosure, antifouling agents which are named for a particular chemical moiety (for example, a "sulfonate antifouling agent" or a "phosphonium antifouling agent") comprise at least one of that particular chemical moiety but may include additional chemical moieties. For example, a "sulfonate antifouling agent" is an antifouling agent which includes a sulfonate moiety and a "phosphonium antifouling agent" is an antifouling agent which includes a phosphonium moiety.

In one or more embodiments, the antifouling catalyst system comprises one or more phosphonium antifouling agents. As used in this disclosure, phosphonium antifouling agents include any compound comprising the phosphonium structure depicted in Chemical Structure #1, where $R_1$, $R_2$, $R_3$, and $R_4$ represents chemical groups which may contain other moieties, and the various R groups may be identical or different from one another. Generally, phosphonium antifouling agents may be introduced into the antifouling catalyst system as phosphonium salts, where the phosphonium cation forms an ionic bond with an anion compound. As used in this disclosure, phosphonium antifouling agents include phosphonium salts or dissociated phosphonium cations.

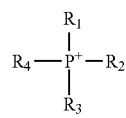

Chemical Structure #1—Generalized Phosphonium Cation

Suitable phosphonium antifouling agents include, without limitation, tetraalkyl phosphonium salts. For example, the antifouling agent may include tetraalkyl phosphonium halides (such as, for example, tetrabutyl phosphonium halide), phosphonium malonates (such as, for example, tetrabutylphosphonium malonate), trihexyltetradecylphosphonium halides (such as, for example, trihexyltetradecylphsophonium bromide), tetrabutylphosphonium halides (such as for example, tetrabutylphosphonium iodide), tetrabutylphosphonium tetrahaloborates (such as, for example, tetrabutylphosphonium tetratluoroborate), tetrabutylphosphonium halides (such as, for example, tetrabutylphosphonium chloride), tetrabutylphosphonium hexahalophosphates (such as, for example, tetrabutylphosphonium hexafluorophosphate), or tetrabutylphosphonium tetrahaloborates (such as, for example, tetrabutylphosphonium tetrafluoroborate). As used throughout this disclosure, a halide may include fluoride, chloride, bromide, or iodide (and "halo" may include the elements fluorine, chlorine, bromine, or iodine). in one or more embodiments, the R groups (that is, $R_1$, $R_2$, $R_3$, and $R_4$) may be branched or unbranched alkanes, alkenes, or aryls, and the R groups may be identical or different from one another.

In one or more embodiments, the antifouling catalyst system comprises one or more sulfonate antifouling agents. As used in this disclosure, sulfonate antifouling agents include any compound comprising the structure depicted in Chemical Structure #2, where R represents a chemical group, which may contain other moieties. Generally, sulfonate antifouling agents may be introduced into the antifouling catalyst system as a sulfonate salt, where the sulfonium anion forms an ionic bond with a cation compound. As used in this disclosure, sulfonium antifouling agents include sulfonium salts or dissociated sulfonium anions.

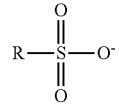

Chemical Structure #2—Generalized Sulfonate Anion

Suitable sulfonate antifouling agents include, without limitation, sulfonate salts. For example, sulfonate antifouling agents may include, without limitation, sodium dodecylbenzenesulfonate, sodium dioctylsulfonsuccinate, tetrabutylphosphonium methanesulfonate, tetrabutylphosphonium p-toluenesulfonate, and hexadecyltrimethylammonium p-toluene sulfonate. In other embodiments, suitable antifouling agents may include non-salt sulfonates (that is, sulfonates which do not dissociate as salts), such as ammonium sulfonates. For example, non-salt sulfonates suitable as antifouling agents include, without limitation, 3-(dimethyl(octadecyl)ammonio)propane-1-sulfonate, 3,3'-(1,4-didodecylpiperazine-1,4-diium-1,4-diyl)bis(propane-1-sulfonate), and 3-(4-(tert-butyl)pyridinio)-1-propanesulfonate.

In one or more embodiments, the antifouling catalyst system comprises one or more sulfonium antifouling agents. Sulfonium antifouling agents are generally depicted in Chemical Structure #3, where $R_1$, $R_2$, and $R_3$ represent chemical groups which may contain other moieties, and the various R groups (that is, $R_1$, $R_2$, and $R_3$) may be identical or different from one another. Generally, sulfonium antifouling agents may be introduced into the antifouling catalyst system as sulfonium salts, where the sulfonium cation forms an ionic bond with an anion compound. As used in this disclosure, sulfonium antifouling agents include sulfonium salts or dissociated sulfonium cations.

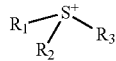

Chemical Structure #3—Generalized Sulfonium Cation

In another embodiment, the antifouling agent may include an ester antifouling agent or an anhydride antifouling agent where, in some embodiments, the ester or anhydride antifouling agent comprises a cyclic moiety. Suitable ester or anhydride antifouling agents which contain a cyclic moiety may include, without limitation, ε-caprolactone, 2-phenylethyl acetate, and polyisobutenyl succinic anhydride. In some embodiments, the ester or anhydride moiety is included in the cyclic moiety. However, in other embodiments, the ester or anhydride moiety is separate from the cyclic moiety. Example cyclic moieties include, without limitation, cyclic alkyls, and aryls, but may include any chemical moiety which includes a ringed structure of atoms. In some embodiments, the ester or anhydride antifouling agent may be an ester or anhydride-capped polymer that has a number average molecular weight (Mn) of from 150 grams per mole (g/mol) to 200,000 g/mol (for example, from 150 g/mol to 1,000 g/mol, from 150 g/mol to 2,000 g/mol, from 150 g/mol to 3,000 g/mol, from 150 g/mol to 5,000 g/mol, from 150 g/mol to 10,000 g/mol, from 150 g/mol to 50,000 g/mol, from 150 g/mol to 100,000 g/mol, from 150 g/mol to 150,000 g/mol, from 1,000 g/mol to 200,000 g/mol, from 5,000 g/mol to 200,000 g/mol, from 10,000 g/mol to 200,000 g/mol, from 50,000 g/mol to 200,000 g/mol, or from 100,000 g/mol to 200,000 g/mol).

In another embodiment, the antifouling agent may include one or more polyether antifouling agents. The polyether antifouling agents may include monomer units comprising carbon chains with one, two, three, four, or even more carbons separating ether moieties. For example, one polyether contemplated in this disclosure includes that depicted in Chemical Structure #4, where m is equal to from 1 to 10 (for example, 1, 2, 3, 4, 5, 6, 7, 8, 9, or 10, or even more, such as m equal to at least 10, at least 25, at least 50, or at least 75, and less than or equal to 100), and n is from 1 to 50,000. R in Chemical Structure 4 may represent a hydrogen atom, or an alkyl with or without branches or substitutions. In embodiments, R may include at least 5, at least 10, or even more carbon atoms). For example, a suitable polyether antifouling agent may be polytetrahydrofuran (where m=4). According to one or more embodiments, the polyether antifouling agent may have a number average molecular weight. (Mn) of from 150 grams per mole (g/mol) to 200,000 g/mol (for example, from 150 g/mol to 1,000 g/mol, from 150 g/mol to 2,000 g/mol, from 150 g/mol to 3,000 g/mol, from 150 g/mol to 5,000 g/mol, from 150 g/mol to 10,000 g/mol, from 150 g/mol to 50,000 g/mol, from 150 g/mol to 100,000 g/mol, from 150 g/mol to 150,000 g/mol, from 1,000 g/mol to 200,000 g/mol, from 5,000 g/mol to 200,000 g/mol from 10,000 g/mol to 200,000 g/mol, from 50,000 g/mol to 200,000 g/mol, or from 100,000 g/mol to 200,000 g/mol)

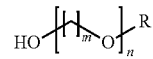

Chemical Structure #4—Example Polyether Antifouling Agent

In another embodiment, the antifouling agent may include one or more long-chained amine-capped antifouling agents. In one or more embodiments, the long-chained amine-capped antifouling agent may have a number average molecular weight (Mn) of from 150 grams per mole (g/mol) to 200,000 g/mol (for example, from 150 g/mol to 1,000 g/mol, from 150 g/mol to 2,000 g/mol, from 150 g/mol to 3,000 g/mol, from 150 g/mol to 5,000 g/mol, from 150 g/mol to 10,000 g/mol, from 150 g/mol to 50,000 g/mol, from 150 g/mol to 100,000 g/mol, from 150 g/mol to 150,000 g/mol, from 1,000 g/mol to 200,000 g/mol, from 5,000 g/mol to 200,000 g/mol, from 10,000 g/mol to 200,000 g/mol, from 50,000 g/mol to 200,000 g/mol or from 100,000 g/mol to 200,000 g/mol). Suitable long-chained amine-capped antifouling agent include, without limitation, polyisobutene-mono-succinimide and polyisobutene-bis-succinimide.

It should be understood that while some embodiments may contain an antifouling agent that is a single chemical species, in other embodiments, two or more different antifouling agent species may be present as the antifouling agent. In embodiments, two or more different antifouling agent species of the same type may be present. For example, the catalyst system may comprise two different species of phosphonium, two different species of sulfonate, two different species of sulfonium, two different species of esters, an anhydride, two different species of polyethers, or two different species of long-chained amine-capped compounds. In additional embodiments, the catalyst system may comprise two or more different types of antifouling agents (that is, two or more of any of a phosphonium or phosphonium salt, a sulfonate or a sulfonate salt, a sulfonium or sulfonium salt, an ester comprising a cyclic moiety, an anhydride, a polyether, and a long-chained amine-capped compound).

Some antifouling agent species may include two or more types of antifouling agents. For example, salts which have an anion of one type of antifouling agent and a cation of a different antifouling agent may generally comprise two types of antifouling agents. Examples of such antifouling agents include tetrabutylphosphonium methanesulfonate and tetrabutylphosphonium p-toluenesulfonate, which are salts that include a sulfonate and a phosphonium.

In one or more embodiments, the antifouling catalyst system may comprise one or more non-polymeric ether compounds. The one or more ether compounds may include cyclic non-polymeric ethers such as, but not limited to, tetrahydrofuran (THF), a dioxane, a tetrahydropyran (THP), or combinations thereof. As used in this disclosure, "non-polymeric" ethers refer to compounds which include one or more ethers but do not include long ether polymer chains. Usually, these non-polymeric ethers comprise one or two ether moieties, and comprise less than 10 ether moieties. While the antifouling catalyst systems described in this disclosure do not require an ether compound in all embodiments, antifouling catalyst systems which include esters or anhydrides as antifouling agents may be particularly suited for not including an ester. It is believed that the ester or anhydride functionalities of some antifouling agents may at least partially replicate or mimic the functionality of ethers in the antifouling catalyst systems, rendering some embodiments of antifouling catalyst systems which include esters or anhydrides sufficient for their purpose without an additional ether compound.

The antifouling catalyst systems may comprise at least one or more titanate compounds, one or more aluminum compounds, and one or more antifouling agents. In one or more embodiments, the molar ratio of total titanate compound to total aluminum compound may be from 1:10 to 1:1 (such as, for example, from 1:10 to 1:2, from 1:10 to 1:3, from 1:10 to 1:4, from 1:10 to 1:5, from 1:10 to 1:6, from 1:10 to 1:7, from 1:10 to 1:8, from 1:10 to 1:9, from 1:9 to 1:1, from 1:8 to 1:1, from 1:7 to 1:1, from 1:6 to 1:1, from 1:5 to 1:1, from 1:4 to 1:1, from 1:3 to 1:1, or from 1:2 to 1).

In one or more embodiments, the molar ratio of total titanate compounds to total antifouling agent may be from 1:10 to 1:0.01 (such as, for example, from 1:10 to 1:0.05, from 1:10 to 1:0.1, from 1:10 to 1:0.3, from 1:10 to 1:0.5, from 1:10 to 1:0.7, from 1:10 to 1:1, from 1:10 to 1:2, from 1:10 to 1:3, from 1:10 to 1:5, from 1:5 to 1:0.01, from 1:3 to 1:0.01, from 1:2 to 1:0.01, from 1:1 to 1:0.01, from 1:0.7 to 1:0.01, or from 1:0.3 to 1:0.01).

In one or more embodiments, the molar ratio of total titanate compounds to total non-polymeric ether compounds may be from 1:10 to 1:0 (such as, for example, from 1:5 to 1:0, from 1:3 to 1:0, from 1:2 to 1:0, from 1:1 to 1:0, from 1:0.5 to 1:0, from 1:0.3 to 1:0, from 1:0.1 to 1:0, from 1:10 to 1:0.1, from 1:10 to 1:0.5, from 1:10 to 1:1, from 1:10 to 1:2, or from 1:10 to 1:5).

It should be understood that the molar ratios of components of the antifouling catalyst systems described previously in this disclosure are representative of the total amount of each component of the antifouling catalyst system relative to the total amount of titanate compound, where the "total" amount refers to the molar amount of all species of the antifouling catalyst system which may be considered as a particular component type (that is, titanate compound, aluminum compound, non-polymeric ether compound, or antifouling agent). The total amount of a component may include two or more chemical species which are titanate compounds, aluminum compounds, non-polymeric ether compounds, or antifouling agents, respectively.

According to another embodiment of the present disclosure, 1-butene may be produced by contacting ethylene with the antifouling catalyst system described previously to oligomerize the ethylene to form 1-butene. In one or more embodiments, the ethylene and antifouling catalyst system are supplied to a reactor and mixed. The reaction may be performed as a batch reaction or as a continuous process reaction, such as a continuous stir tank reactor process. According to further embodiments, the pressure of the reactor may be from 5 bar to 100 bar, and the reactor temperature may be from 30 degrees Celsius (° C.) to 180° C. However, process conditions outside of these ranges are contemplated, especially in view of the specific design of the reactor system and concentrations of the reactants and catalysts. The reactions of the present disclosure primarily limit or do not include polymerization of ethylene (for example, polymers comprising 100 or more monomer ethylene units). In embodiments, polymer formation may be limited to less than 500, less than 300, or even less than 100 parts per million of reactant.

In one or more embodiments, without being bound by theory, it is believed that heteroatoms of the antifouling agents may form weak coordination with the titanate compound utilized as the catalyst in the catalyst system. It is believed that, in one or more embodiments, the alkyl groups or other relatively long-chained groups of the antifouling agents may serve in some capacity to prevent ethylene access to the catalytic center of the titanate compound. The restriction of access of the ethylene to the titanate catalytic site may reduce the polymerization of ethylene and thus reduce reactor fouling.

In one or more embodiments, the introduction of the antifouling agent into a catalyst system may suppress polymer formation while not greatly reducing catalytic activity of 1-butene formation, in one embodiment, polymer formation (fouling) may be reduced by at least 5%, 10%, 20%, 30%, 40%, 50%, 60%, 70%, 80%, 90%, or even 95% by the inclusion of an antifouling agent. In one embodiment, 1-butene production may be increased, stay the same, or may decrease by less than or equal to 50%, 40%, 30%, 20%, 10% or even 5% by the inclusion of an antifouling agent. In some embodiments, antifouling agents may both reduce the polymer formation (such as by at least 5%, 10%, 20%, 30%, 40%, 50%, 60%, 70%, 80%, 90% or even 95%) and increase, not effect, or decrease 1-butene production rate by less than or equal to 50%, 40%, 30%, 20%, 10% or even 5%. Reduction in polymer formation rates and catalytic activity on a percentage basis are based on catalyst systems which include one or more antifouling agents described as compared with catalyst systems which are void of an antifouling agent.

Examples

The various embodiments of antifouling catalyst systems will be further clarified by the following examples. The examples are illustrative in nature, and should not be understood to limit the subject matter of the present disclosure.

To evaluate the anti-fouling effects of the antifouling catalyst systems described, ethylene oligomerization reactions were carried out and evaluated. Multiple sample antifouling catalyst systems were formulated which had different antifouling agents or no additional antifouling agent (as a control sample listed as "Comparative Example in Table 1). For the experiments, catalyst mixtures were used that contained titanium tetrabutoxide (denoted as "Ti" in Table 1), THF, triethyl aluminum (sometimes referred to as "TEAL"), and antifouling agents (denoted as "AFA" in Table 1). The molar ratio of Ti:AFA for each example is listed in Table 1. The molar ratio of Ti:THF:TEAL in the examples was 1:6:7.5. The oligomerization experiments were conducted in a rig which included 8 autoclave reactors each having a volume of 400 milliliters (mL). Prior to the experimental runs, the rig was subjected to inertization process which included evacuating the reactors with an oil vacuum pump and heating to 160° C. After a stable temperature had been reached, the rig was pressurized to 4 bar with nitrogen and the stirrers were operated with a stirring speed of about 300 rpm. Then, three minutes following the start of the pressurization, the gas outlet valves were opened to release the nitrogen to the exhaust. Two minutes after the gas release had started, the valves from the main exhaust pipe to the vacuum pump were opened to evacuate the rig. The rig was evacuated for 15 minutes. The gas outlet valves were then closed, and the rig was pressurized with nitrogen again. The pump-pressurize cycles were run for at least 30 hours. The rig was then evacuated in vacuum for a further 6 to 8 hours. During the last one hour, the autoclave reactors were cooled down to 45° C. The rig was then pressurized to 3 bar until the reaction was started.

Chargers were prepared, which included the components of the catalyst mixtures. To prepare the chargers, two stock solutions were prepared in a glove box. Heptane was utilized as a solvent, and an amount of heptane was utilized, such that the autoclave reactors were nominally filled. The first solution contained the TEAL co-catalyst mixed with 90% of the heptane. The second solution contained the titanium tetrabutoxide catalyst, the THF, and the antifouling agents mixed with 10% of the heptane. The first solution and the second solution were put into first solution chargers and second solution chargers, respectively.

To run the oligomerization experiment, the pressure in the rig was released to about 0.2 bar. The chargers with the second solution of TEAL/heptane were injected into the reactors. The charging was achieved by pressurizing the chargers with ethylene to 10 bar and opening the valve between the charger and the reactor. The contents of the second solution charger were then injected, using ethene as the charging gas with a pressure of 35 bar. The target pressure for the reactors was set to 23 bar. The gas dosage into the reactor was started automatically. The temperature in the reactor rose and the temperature was set to the target value of 53.5° C. After the start of the ethene dosage, the reaction was run for 75 min.

After 75 minutes of reaction time, the reaction was terminated by the injection of 1 mL of ethanol. The pressure was released from the reactors, and the temperature was set to 20° C. The reactors were opened and the contents of the reactor, including the baffles and stirrers, were removed and placed in a heating oven at 75° C. for one hour. The residue in the reactor was then washed with a 10 wt. % aqueous sulfuric acid solution to dissolve any catalyst residues. The remaining solid polymer was filtered and dried overnight in an oven at 110° C. and weighed.

Table 1 shows the dimerization activity and weight of polymer deposit for reactions which utilized each of the sample catalyst systems. As is evident by the reaction data of Table 1, the addition of the anti-fouling additives reduced polymer formation to some degree while maintaining relatively high dimerization activity.

TABLE 1

| Experiment Number | Molar Ratio of Ti:AFA | Activity (grams of ethylene per hour per millimoles of titanium) | Polymer Produced in parts per million (and in mg) | AFA chemical species |
|---|---|---|---|---|
| Comparative Example | 1:0 | 228 | 1,310 (149) | N/A |
| Example #1 | 0.3:1 | 237 | 55 (6.5) | tetrabutylphosphonium bromide |
| Example #2 | 0.3:1 | 9 | 0 (0) | tetrabutylphosphonium malonate |
| Example #3 | 0.3:1 | 216 | 97 (8) | sodium dodecylbenzenesulfonate |
| Example #4 | 3:1 | 208 | 96 (10) | sodium dodecylbenzenesulfonate |
| Example #5 | 0.3:1 | 166 | 187 (36) | sodium dioctylsulfonsuccinate |
| Example #6 | 0.3:1 | 242 | 99 (12) | 3-(dimethyl(octadecyl)ammonio)propane-1-sulfonate |
| Example #7 | 0.3:1 | 234 | 145 (17) | 3,3'-(1,4-didodecylpiperazine-1,4-diium-1,4-diyl)bis(propane-1-sulfonate) |
| Example #8 | 0.3:1 | 229 | 289 (33) | 3-(4-(tert-butyl)pyridinio)-1-propanesulfonate |
| Example #9 | 0.3:1 | 226 | 354 (40) | 1,4-didodecylpiperazine |
| Example #10 | 0.3:1 | 230 | 228 (32) | 2-phenylethyl acetate |
| Example #11 | 0.3:1 | 185 | 141 (13) | polyisobutenyl succinic anhydride |
| Example #12 | 0.3:1 | 233 | 343 (40) | Polyether (Polytetrahydrofuran with Mn = 1100) |
| Example #13 | 0.3:1 | 238 | 210 (25) | hexadecyltrimethylammonium p-toluene sulfonate |
| Example #14 | 0.3:1 | 201 | 676 (68) | ε-caprolactone |

As is shown from Table 1, a number of tested antifouling agents reduced the polymer produced while not greatly reducing the catalytic activity. Table 2 depicts data regarding the reduction in activity and the reduction in polymer produced based on the change observed between the Comparative Example (which did not include an antifouling agent) to each example which included an antifouling additive.

TABLE 2

| Experiment Number | Activity Reduction (Negative is Activity Increase) | Polymer Formation Reduction |
|---|---|---|
| Comparative Example | 0.0% | 0.0% |
| Example #1 | −3.9% | 95.8% |
| Example #2 | 96.1% | 100.0% |
| Example #3 | 5.3% | 92.6% |
| Example #4 | 8.8% | 92.7% |
| Example #5 | 27.2% | 85.7% |
| Example #6 | −6.1% | 92.4% |
| Example #7 | −2.6% | 88.9% |
| Example #8 | −0.4% | 77.9% |
| Example #9 | 0.9% | 73.0% |
| Example #10 | −0.9% | 82.6% |
| Example #11 | 18.9% | 89.2% |
| Example #12 | −2.2% | 73.8% |
| Example #13 | −4.4% | 84.0% |
| Example #14 | 11.8% | 48.4% |

As is shown in Table 2, a number of antifouling agents suppress polymer formation (for example, at least 5%, 10%, 20%, 30%, 40%, 50%, 60%, 70%, 80%, 90% or even 95% reduction) while not greatly reducing activity (for example, less than or equal to 50%, 40%, 30%, 20%, 10% or even 5% reduction in activity, or even increased activity).

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various embodiments described herein. Further, it will be apparent that modifications and variations are possible without departing from the scope of the appended claims.

What is claimed is:

1. A catalyst that reduces polymeric fouling, the catalyst system comprising:
   at least one titanate compound;
   at least one aluminum compound; and
   an antifouling agent, where the antifouling agent is an ester comprising a cyclic moiety;
   wherein a molar ratio of total titanate compound to total aluminum compound is from 1:10 to 1:1, where the antifouling agent comprises one or more of ε-caprolactone and 2-phenylethyl acetate, and where a molar ratio of total titanate compound to total antifouling agent is from 1:10 to 1:0.01.

2. The catalyst of claim 1, further comprising a non-polymeric ether compound.

3. The catalyst of claim 2, the non-polymeric ether compound is tetrahydrofuran, a dioxane, or tetrahydropyran.

4. The catalyst of claim 2, a molar ratio of total titanate compound to total non-polymeric ether compound is from 1:10 to 1:0.1.

5. The catalyst of claim 1, where at least one of the titanate compounds is an alkyl titanate.

6. The catalyst of claim 5, where the alkyl titanate has the structure $Ti(OR)_4$, where R is a branched or straight chain alkyl radical comprising from 2 to 8 carbon atoms.

7. The catalyst of claim 5, where the alkyl titanate is chosen from tetraethyl titanate, tetraisopropyl titanate, tetra-n-butyl titanate, or 2-tetraethylhexyl titanate.

8. The catalyst of claim 1, where at least one of the aluminum compounds has the structure $AlR'_3$ or $AlR'_2H$, where R' is a branched or straight chain alkyl radical comprising from 2 to 8 carbon atoms.

9. The catalyst of claim 1, where at least one of the aluminum compounds is chosen from triethylaluminum, tripropylaluminum, tri-iso-butylaluminum, trihexylaluminum, or an aluminoxane.

10. A method for selectively producing 1-butene, the method comprising:
    contacting ethylene with the catalyst of claim 1 to oligomerize the ethylene to selectively form 1-butene, where the catalyst comprises:
    at least one titanate compound;
    at least one aluminum compound; and
    an antifouling agent, where the antifouling agent is an ester comprising a cyclic moiety;
    wherein a molar ratio of total titanate compound to total aluminum compound is from 1:10 to 1:1, where the antifouling agent comprises one or more of s-caprolactone and 2-phenylethyl acetate, and where a molar ratio of total titanate compound to total antifouling agent is from 1:10 to 1:0.01.

11. The method of claim 10, further comprising a non-polymeric ether compound.

12. The method of claim 10, where at least one of the titanate compounds is an alkyl titanate.

13. The method of claim 12, where the alkyl titanate has the structure $Ti(OR)_4$ where R is a branched or straight chain alkyl radical comprising from 2 to 8 carbon atoms.

14. The method of claim 10, where at least one of the aluminum compounds has the structure $AlR'_3$ or $AlR'_2H$, where R' is a branched or straight chain alkyl radical comprising from 2 to 8 carbon atoms.

* * * * *